United States Patent
Breuner et al.

(10) Patent No.: US 11,174,487 B2
(45) Date of Patent: Nov. 16, 2021

(54) STABLE GENOMIC INTEGRATION OF MULTIPLE POLYNUCLEOTIDE COPIES

(71) Applicant: Novozymes A/S, Bagsvaerd (DK)

(72) Inventors: Anne Breuner, Klampenborg (DK); Michael Dolberg Rasmussen, Vallensbaek (DK)

(73) Assignee: Novozymes A/S, Bagsvaerd (DK)

( * ) Notice: Subject to any disclaimer, the term of this patent is extended or adjusted under 35 U.S.C. 154(b) by 235 days.

(21) Appl. No.: 15/481,879

(22) Filed: Apr. 7, 2017

(65) Prior Publication Data

US 2017/0218381 A1    Aug. 3, 2017

Related U.S. Application Data

(63) Continuation of application No. 14/221,005, filed on Mar. 20, 2014, which is a continuation of application No. 11/576,896, filed as application No. PCT/DK2005/000673 on Oct. 19, 2005, now abandoned.

(60) Provisional application No. 60/630,715, filed on Nov. 23, 2004, provisional application No. 60/621,896, filed on Oct. 25, 2004.

(30) Foreign Application Priority Data

Oct. 22, 2004  (DK) ................................ 2004 01621
Nov. 17, 2004  (DK) ................................ 2004 01785

(51) Int. Cl.
*C12N 15/75* (2006.01)
*C12N 15/10* (2006.01)
*C12N 15/90* (2006.01)

(52) U.S. Cl.
CPC ......... *C12N 15/75* (2013.01); *C12N 15/1082* (2013.01); *C12N 15/1086* (2013.01); *C12N 15/90* (2013.01); *C12N 15/902* (2013.01); *C12N 2800/30* (2013.01); *C12N 2830/50* (2013.01)

(58) Field of Classification Search
None
See application file for complete search history.

(56) References Cited

U.S. PATENT DOCUMENTS 5,955,310 A * 9/1999 Widner .................. C12N 15/75
                                                                435/183
6,017,694 A   1/2000 Mak et al.
9,574,199 B2 * 2/2017 Udagawa ................ C12P 21/02

FOREIGN PATENT DOCUMENTS

| EP | 0166628 A1 | 1/1986 | |
| EP | 0284126 A1 | 9/1988 | |
| EP | 1405908 A1 | 4/2004 | |
| WO | 95/17499 A1 | 6/1995 | |
| WO | 99/43835 A2 | 9/1999 | |
| WO | 00/05355 A1 | 2/2000 | |
| WO | 02/00907 A1 | 1/2002 | |
| WO | 02/08409 A2 | 1/2002 | |
| WO | WO-0208409 A2 * | 1/2002 | ......... C12N 15/8213 |
| WO | 2004/018635 A2 | 3/2004 | |
| WO | 2004/056973 A2 | 7/2004 | |
| WO | WO-2006042548 A1 * | 4/2006 | ........... C12N 15/902 |

OTHER PUBLICATIONS

Anonymous, NCBI webpage download Jun. 30, 2010.
Boyd et al., Journal of Bacteriology, vol. 182, No. 3, pp. 842-847 (Feb. 2000).
Breuner et al., Microbiology, vol. 147, pp. 2051-2063 (2001).
Datsenko et al., PNAS, vol. 97, No. 12, pp. 6640-6645 (2000).
Ellermeier et al., Gene, vol. 290, Nos. 1-2, pp. 153-161 (May 15, 2002).
Haldimann, Journal of Bacteriology, vol. 183, No. 21, pp. 6384-6393 (Nov. 2001).
Ho et al., Protein Expression and Purification, vol. 32, No. 2, pp. 293-301 (Dec. 2003).
Itaya, Molecular Gene Genetics, vol. 248, pp. 9-16 (1995).
Lee et al., Biotechnol. Prog., vol. 13, pp. 368-373 (1997).
Nasvall et al., RNA, vol. 10, pp. 1662-1673 (2004).
Smith et al., Molecular Microbiology, vol. 51, No. 6, pp. 1719-1728 (2004).
Solem et al., Applied and Environmental Microbiology, vol. 68, No. 5, pp. 2397-2403 (May 2002).
Wegmann et al., GenBank Accession No. AM406671.1 (2006).
Zhang et al., EMBL Accession No. AJ237900 (1998).

* cited by examiner

*Primary Examiner* — Suzanne M Noakes
*Assistant Examiner* — Jae W Lee
(74) *Attorney, Agent, or Firm* — Eric J. Fechter

(57) ABSTRACT

Methods of constructing a cell comprising in its chromosome one or more copies of an open reading frame (ORF) or operon encoding at least one polypeptide of interest, each copy being under the transcriptional control of a heterologous promoter using a site specific recombinase and in vivo integration by recombination; resulting cells, and methods for producing a polypeptide of interest using the resulting cells.

Figure 1:
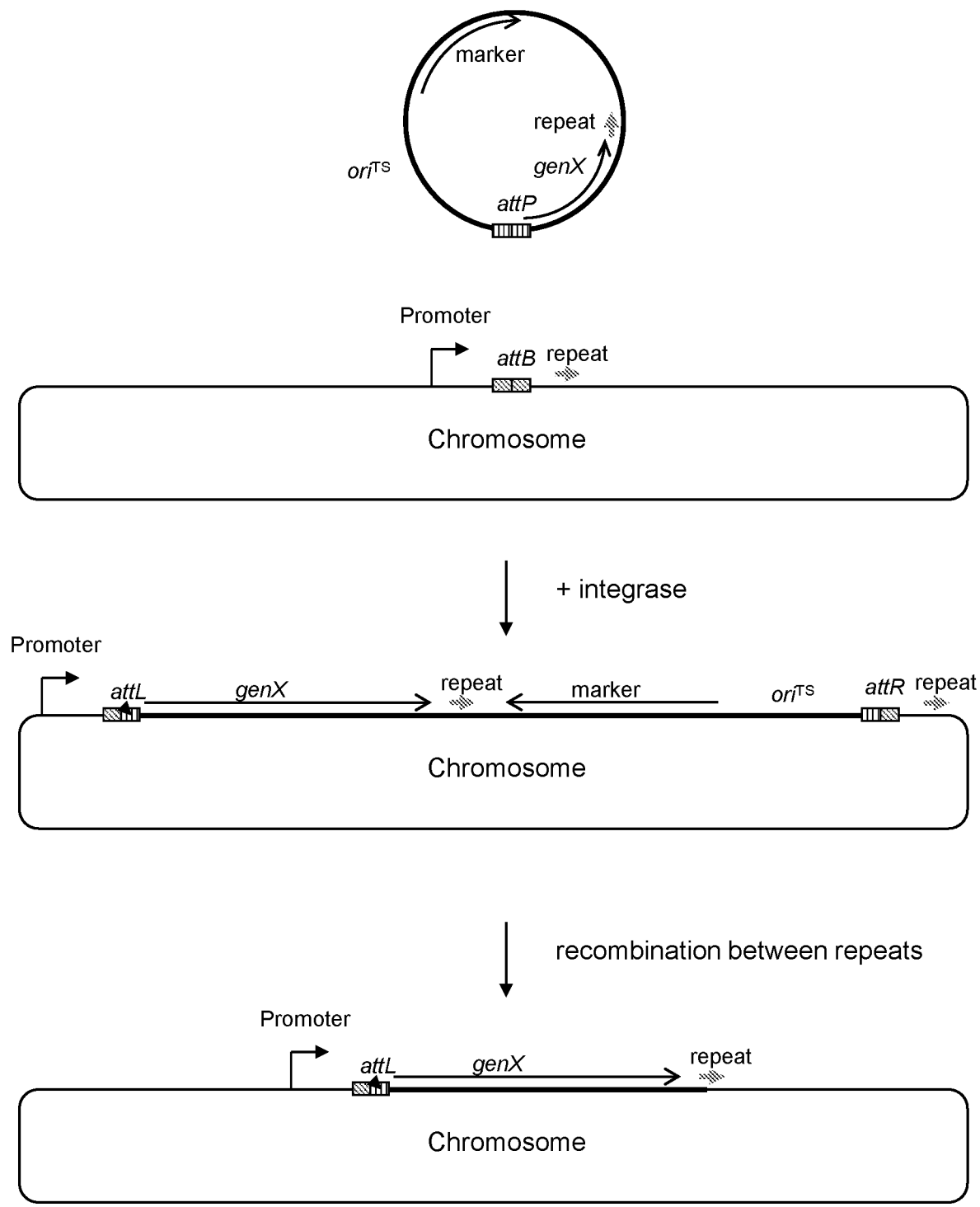

23 Claims, 2 Drawing Sheets
Specification includes a Sequence Listing.

STABLE GENOMIC INTEGRATION OF MULTIPLE POLYNUCLEOTIDE COPIES

CROSS-REFERENCE TO RELATED APPLICATIONS

This application is a continuation of U.S. application Ser. No. 14/221,005 filed on Mar. 20, 2014, now abandoned, which is a continuation of U.S. application Ser. No. 11/576,896 filed on Apr. 9, 2017, now abandoned, which is a 35 U.S.C. 371 national application of international application no. PCT/DK2005/000673 filed on Oct. 19, 2005, which claims priority or the benefit under 35 U.S.C. 119 of Danish application nos. PA 2004 01621 and PA 2004 01785 filed Oct. 22, 2004 and Nov. 17, 2004, respectively, and U.S. provisional application Nos. 60/621,896 and 60/630,715 filed Oct. 25, 2004 and Nov. 23, 2004, respectively. The contents of these applications are fully incorporated herein by reference.

FIELD OF THE INVENTION

A large number of naturally-occurring organisms have been found to produce useful polypeptide products, e.g., enzymes, the large scale production of which is desirable for research and commercial purposes. Once such product has been identified efforts are being made to develop production methods leading to a high production of the product. One widely used method, which is based on recombinant DNA techniques, is to clone a gene encoding the product, inserting the gene into a suitable expression system permitting the expression of the product and culturing a suitable host cell comprising the expression system, either integrated in the chromosome or as an extrachromosomal entity, under conditions conducive for the expression of the product.

Irrespective of which production method is used, it is normally desirable to be able to increase the production level of a given polypeptide or protein. Thus, efforts are being made to increase the production, e.g., by inserting the gene encoding the product under the control of a strong expression signal, or by increasing the number of copies of the gene in the production organism in question. This latter approach may be accomplished by inserting the gene into a multicopy plasmid which generally, however, tends to be unstable in the host cell in question, or by integrating multiple copies of the gene into the chromosome of the production organism, an approach which generally is considered more attractive because the stability of the construct tend to be higher allowing the gene to be stably maintained in the production organism.

BACKGROUND OF THE INVENTION

EP 0 284 126 and EP 0 166 628 disclose methods for stably integrating one or more copies of a gene into the chromosome of a prokaryotic cell already harbouring at least one copy of the gene in question in its chromosome. According to EP 0 284 126, a host cell comprising said gene is transformed with a DNA construct comprising another copy of the gene, whereby, after a suitable selection procedure, a cell is obtained which in its chromosome comprises two copies of the gene separated by an endogenous chromosomal sequence which is vital to the host cell and thereby ensures stable maintenance of the integrated gene. This procedure may be repeated so as to produce cells harboring multiple copies of the gene in its chromosome. WO 02/00907 describes methods to site-specifically integrate polynucleotides into inactivated chromosomal loci that are conditionally essential to the cell, where these loci are restored by the integration process.

It has been shown that infection of host cells having a natural attachment site, attB as well as an ectopically introduced attB site, with a derivative of the *Streptomyces* phage ΦC31, resulted in the integration of the phage into both attB sites (Smith et al., 2004. "Switching the polarity of a bacteriophage integration system", *Mol. Microbiol.* 51(6): 1719-1728).

In fact, multiple copies of a gene can be introduced into a cell comprising multiple attachment sites recognized by the Mx9 integrase using the Mx9 phage transformation system, (WO 2004/018635).

SUMMARY OF THE INVENTION

It may often be difficult to achieve proper chromosomal integration in a host cell of a gene encoding a polypeptide of interest, when the gene is introduced into the cell on a DNA construct, even a low-copy number construct, while being actively transcribed from a promoter on the construct. This is particularly true for polypeptides that are inhibitory or perhaps even toxic to the host cell above a certain concentration. One way of avoiding this problem is to silence the gene while it is on the construct, so that transcription is only initiated when the gene has been properly integrated into the chromosome.

Usually it of interest to integrate several copies of a gene encoding a polypeptide of interest into the host cell chromosome, sometimes up to 10 or more copies. A method for simultaneously integrating the desired number of copies would be time-saving compared with stepwise methods like those mentioned above.

The present invention provides a combined solution to these problems; it allows the simultaneous chromosomal site-specific integration of multiple copies of a gene (or operon) encoding a polypeptide(s) of interest, while also providing the means for initiating transcription of said gene after the proper integration of each copy via a heterologous promoter, which becomes operably linked with the gene only after the successful integration.

Accordingly, in a first aspect, the present invention relates to a method of constructing a cell comprising in its chromosome one or more copies of an open reading frame (ORF) or operon encoding at least one polypeptide of interest, each copy being under the transcriptional control of a heterologous promoter, said method comprising the steps of:

(a) providing a cell comprising in its chromosome one or more copies of a first recognition sequence (RS1) of a site specific recombinase, wherein each copy of RS1 is located downstream of a copy of said heterologous promoter;

(b) introducing into said cell a polynucleotide construct comprising the ORF or operon and a second recognition sequence (RS2) of the site specific recombinase, where RS2 is located and oriented with respect to the ORF or operon so that an in vivo recombination of RS2 with a copy of RS1 in the chromosome of the cell will integrate the construct into the chromosome and place the ORF or operon downstream of and in the same orientation as the heterologous promoter; and (c) recombining RS2 with the one or more copies of RS1 in the presence of the site specific recombinase, whereby one or more copies of the ORF or operon of interest are integrated into the chromosome and placed (i) either directly under the transcriptional control of the heterologous promoter, or (ii) downstream of and in the same orientation as the promoter but separated from it by a region, which can be excised after one or more optional recombination events, whereby the ORF or operon of interest is placed under the transcriptional control of the heterologous promoter.

One of the means for carrying out the invention is a host cell specifically designed for this purpose; the cell has been engineered to comprise one or more copies of a recognition sequence (RS) of a site specific recombinase, as exemplified below, wherein each copy of the RS is located downstream of a copy of a heterologous promoter. This arrangement ensures that when a polynucleotide construct of the invention recombines into the chromosome by the action of the site specific recombinase, the ORF or operon comprised in the construct will be operably linked with the heterologous promoter already present in the chromosome.

Accordingly, in a second aspect, the invention relates to a cell comprising in its chromosome one or more copies of a recognition sequence (RS) of a site specific recombinase, wherein each copy of the RS is located downstream of a copy of a heterologous promoter.

In a third aspect, the invention relates to a cell produced by a method of the first aspect, or a cell comprising in its chromosome one or more copies of an open reading frame (ORF) or operon of interest, wherein each copy is under the transcriptional control of a heterologous promoter, and (i) wherein each copy of the ORF or operon is located in the chromosome upstream of a recognition sequence (RS) of a site specific recombinase, or (ii) wherein each copy of the ORF or operon is located in the chromosome downstream of a recognition sequence (RS) of a site specific recombinase.

Another means for carrying out the invention is of course the polynucleotide construct mentioned in the method of the first aspect.

Consequently, a fourth aspect of the invention relates to a polynucleotide construct comprising a promoterless open reading frame (ORF) or operon encoding at least one polypeptide of interest, the construct also comprising a recognition sequence (RS) of a site specific recombinase located upstream or downstream of said ORF or operon.

In a final aspect, the invention relates to a method of producing a polypeptide of interest, said method comprising:

(a) cultivating a cell of the third aspect or a cell comprising in its chromosome one or more copies of an open reading frame (ORF) or operon of interest, wherein each copy is under the transcriptional control of a heterologous promoter, and (i) wherein each copy of the ORF or operon is located in the chromosome upstream of a recognition sequence (RS) of a site specific recombinase, or (ii) wherein each copy of the ORF or operon is located in the chromosome downstream of a recognition sequence (RS) of a site specific recombinase; and (b) isolating the polypeptide of interest.

FIGURES

Figure 2:
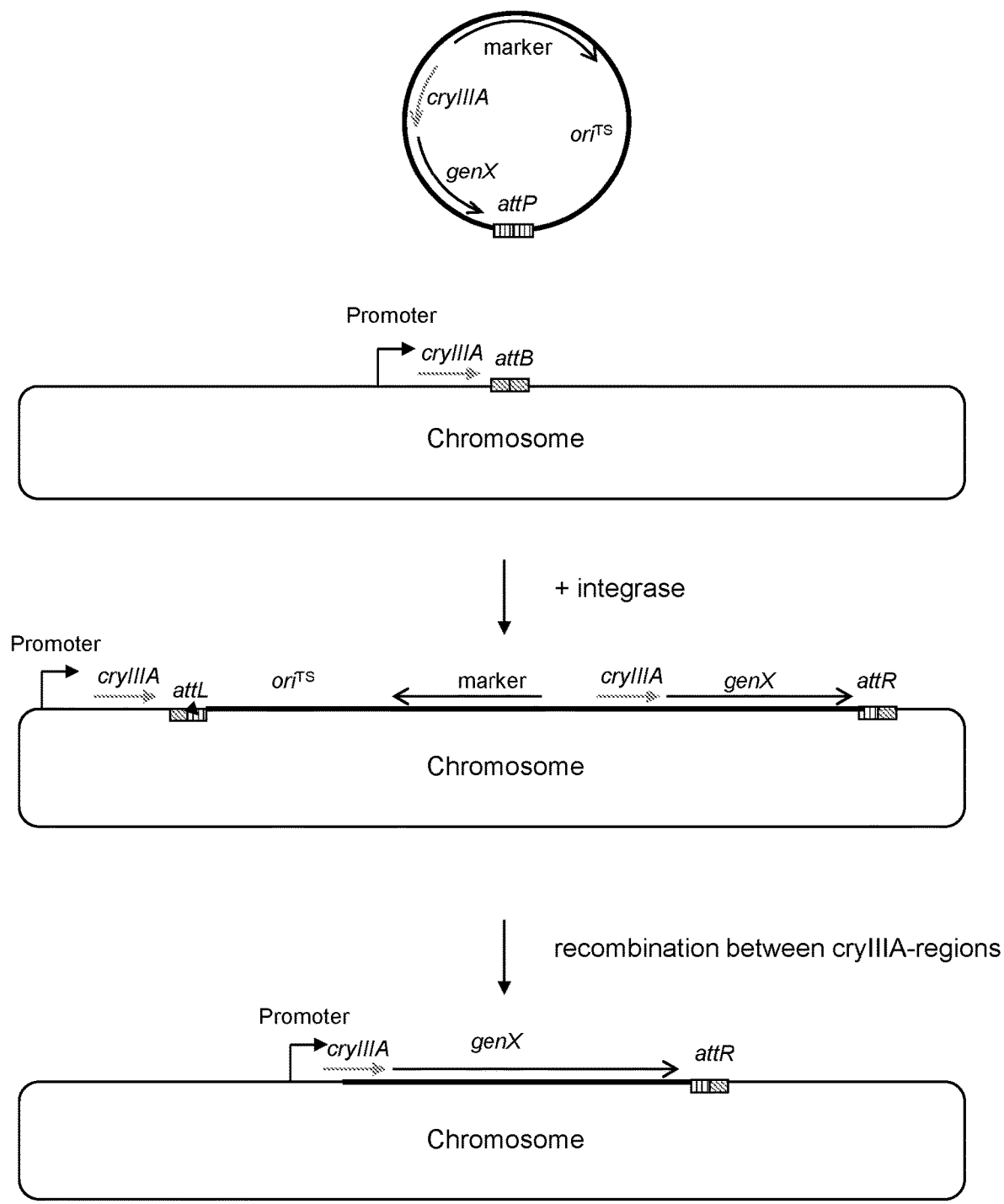

FIGS. 1 and 2. A schematic overview of a preferred embodiment of the invention:

A circular polynucleotide construct comprising the recognition sequense of the TP901-1 phage integrase, attP, located upstream of an open reading frame, genX. The construct further comprises an optional marker, a temperature sensitive origin of replication, ori$^{-TS}$, as well as a region located downstream of the open reading frame in the construct, which is indicated with a small arrow denoted "repeat".

A chromosome of a host cell is also shown comprising a heterologous promoter and the TP901-1 phage integrase recognition sequence, attB, corresponding to the recognition sequence in the construct, which is located downstream of the promoter. In addition, a region is indicated in the chromosome with a small arrow denoted "repeat".

The "repeat" regions of the chromosome and the polynucleotide construct should be sufficiently homologous to effectuate in vivo homologous recombination between the two homologous regions when both regions are present in the cell.

In the presence of a suitable integrase (+ integrase), e.g., the TP901-1 phage integrase, the attP and attB sites are recombined, whereby the construct is integrated into the chromosome, placing the open reading frame, genX, under the transcriptional control of the heterologous promoter, creating the resulting attL and attR sites in the process.

In an optional next step, the two homologous "repeat" regions recombine, whereby the DNA in between the two regions is excised from the chromosome, leaving just the open reading frame, genX, in the chromosome along with the newly created attL site.

DEFINITIONS

For purposes of the present invention, alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is –12 for proteins and –16 for DNA, while the penalty for additional residues in a gap is –2 for proteins and –4 for DNA. Alignment may be made with the FASTA package version v20u6 (Pearson and Lipman, 1988, "Improved Tools for Biological Sequence Analysis", *PNAS* 85:2444-2448, and Pearson, 1990, "Rapid and Sensitive Sequence Comparison with FASTP and FASTA", *Methods in Enzymology* 183:63-98).

Multiple alignments of protein sequences may be made using "ClustalW" (Thompson et al., 1994, "CLUSTAL W: improving the sensitivity of progressive multiple sequence alignment through sequence weighting, positions-specific gap penalties and weight matrix choice", *Nucleic Acids Research* 22:4673-4680). Multiple alignment of DNA sequences may be done using the protein alignment as a template, replacing the amino acids with the corresponding codon from the DNA sequence.

"Promoter" is defined herein as a nucleic acid sequence involved in the binding of RNA polymerase to initiate transcription of a gene. "Tandem promoter" is defined herein as two or more promoter sequences each of which is operably linked to a coding sequence and mediates the transcription of the coding sequence into mRNA. "Operably linked" is defined herein as a configuration in which a control sequence, e.g., a promoter sequence, is appropriately placed at a position relative to a coding sequence such that the control sequence directs the production of a polypeptide encoded by the coding sequence. "Coding sequence" is defined herein as a nucleic acid sequence which is transcribed into mRNA and translated into a polypeptide when placed under the control of the appropriate control sequences. The boundaries of the coding sequence are generally determined by a ribosome binding site located just upstream of the open reading frame at the 5' end of the mRNA and a transcription terminator sequence located just downstream of the open reading frame at the 3' end of the mRNA. A coding sequence can include, but is not limited to, genomic DNA, cDNA, semisynthetic, synthetic, and recombinant nucleic acid sequences.

"Heterologous" DNA in a host cell, in the present context refers to exogenous DNA not originating from the cell.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence.

The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" denotes herein a configuration in which a control sequence is placed at an appropriate position relative to the coding sequence of the polynucleotide sequence such that the control sequence directs the expression of the coding sequence of a polypeptide.

When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

The term "expression" includes any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide of the invention, and which is operably linked to additional nucleotides that provide for its expression.

The term "host cell", as used herein, includes any cell type which is susceptible to transformation, transfection, transduction, and the like with a nucleic acid construct comprising a polynucleotide of the present invention.

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may also be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase,

*Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome.

For integration into the host cell genome, or subsequent excision of parts of the vector, the vector may rely on the polynucleotide's sequence encoding the polypeptide or any other element of the vector for integration into the genome by homologous or nonhomologous recombination. Alternatively, the vector may contain additional nucleotide sequences for directing integration or excision by homologous recombination into or from the genome of the host cell at a precise location(s) in the chromosome(s). To increase the likelihood of integration at or excision from a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla *Ascomycota, Basidiomycota, Chytridiomycota*, and *Zygomycota* (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa,* or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 0 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide.

The present invention also relates to methods for producing a polypeptide of the present invention, comprising (a) cultivating a host cell under conditions conducive for production of the polypeptide; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

DETAILED DESCRIPTION OF THE INVENTION

The first aspect of the invention relates to a method of constructing a cell comprising in its chromosome one or more copies of an open reading frame (ORF) or operon encoding at least one polypeptide of interest, each copy being under the transcriptional control of a heterologous promoter, said method comprising the steps of:

(a) providing a cell comprising in its chromosome one or more copies of a first recognition sequence (RS1) of a site specific recombinase, wherein each copy of RS1 is located downstream of a copy of said heterologous promoter;

(b) introducing into said cell a polynucleotide construct comprising the ORF or operon and a second recognition sequence (RS2) of the site specific recombinase, where RS2 is located and oriented with respect to the ORF or operon so that an in vivo recombination of RS2 with a copy of RS1 in the chromosome of the cell will integrate the construct into the chromosome and place the ORF or operon downstream of and in the same orientation as the heterologous promoter; and (c) recombining RS2 with the one or more copies of RS1 in the presence of the site specific recombinase, whereby one or more copies of the ORF or operon of interest are integrated into the chromosome and placed (i) either directly under the transcriptional control of the heterologous promoter, or (ii) downstream of and in the same orientation as the promoter but separated from it by a region, which can be excised after one or more optional recombination events, whereby the ORF or operon of interest is placed under the transcriptional control of the heterologous promoter.

In the cell of step (a) each copy of RS1 is located downstream of a copy of the heterologous promoter. How far downstream of the promoter RS1 may be located in the cell is a matter of trial and error; the only limiting factor is that the promoter must be operably linked with the ORF or operon after the construct has been integrated into the chromosome. Preferably RS1 is located up to 10,000 bp downstream of the promoter, even more preferably up to 5,000 bp downstram of the promoter, and most preferably no more than 500 bp downstream of the promoter.

Correspondingly, in the polynucleotide construct "RS2 is located and oriented with respect to the ORF or operon so that an in vivo recombination of RS2 with a copy of RS1 in the chromosome of the cell will integrate the construct into the chromosome and bring the ORF or operon under the transcriptional control of the heterologous promoter". This is to ensure that the ORF or operon and RS2 have the correct orientation with respect to each other and with respect to the polarity of RS1 in the chromosome, so that the recombinase mediated recombination between RS1 and RS2 will place the ORF or operon under the transcriptional control of the promoter. RS2 is preferably located up to 10,000 bp upstream of the ORF or operon, even more preferably up to 5,000 bp upstram of the ORF or operon, and most preferably no more than 500 bp upstream of the ORF or operon.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as Gram positive bacteria including, but not limited to, a *Bacillus* cell, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or Gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell.

In a preferred embodiment of any of the aspects of the invention, the cell is a prokaryotic cell, preferably a *Bacillus* cell, and more preferably a *Bacillus subtilis* or a *Bacillus licheniformis* cell.

The ORF or operon in any aspects of the invention preferably encodes at least one enzyme; preferably an oxidoreductase, a transferase, a hydrolase, a lyase, an isomerase, or a ligase; more preferably an amylolytic enzyme, a lipolytic enzyme, a proteolytic enzyme, a cellulytic enzyme, an oxidoreductase or a plant cell-wall degrading enzyme, and most preferably an enzyme with an activity selected from the group consisting of aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, or xylanase.

WO 93/10249 discloses various promoter variants, and WO 99/43835 discloses tandem and triple promoter constructions with improved properties. Each promoter sequence of the tandem promoter may be any nucleic acid sequence which shows transcriptional activity in the *Bacillus* cell of choice including a mutant, truncated, and hybrid promoter, and may be obtained from genes encoding extracellular or intracellular polypeptides either homologous or heterologous to the *Bacillus* cell. Each promoter sequence may be native or foreign to the nucleic acid sequence encoding the polypeptide and native or foreign to the *Bacillus* cell. The promoter sequences may be the same promoter sequence or different promoter sequences.

In a preferred embodiment, the promoter sequences may be obtained from a bacterial source. In a more preferred embodiment, the promoter sequences may be obtained from a gram positive bacterium such as a *Bacillus* strain, e.g., *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis*; or a *Streptomyces* strain, e.g., *Streptomyces lividans* or *Streptomyces murinus*; or from a gram negative bacterium, e.g., *E. coli* or *Pseudomonas* sp.

An example of a suitable promoter for directing the transcription of a nucleic acid sequence in the methods of the present invention is the promoter obtained from the *E. coli* lac operon. Another example is the promoter of the *Streptomyces coelicolor* agarase gene (dagA). Another example is the promoter of the *Bacillus lentus* alkaline protease gene (aprH). Another example is the promoter of the *Bacillus licheniformis* alkaline protease gene (subtilisin Carlsberg gene). Another example is the promoter of the *Bacillus subtilis* levansucrase gene (sacB). Another example is the promoter of the *Bacillus subtilis* alpha-amylase gene (amyE). Another example is the promoter of the *Bacillus licheniformis* alpha-amylase gene (amyL). Another example is the promoter of the *Bacillus stearothermophilus* maltogenic amylase gene (amyM). Another example is the promoter of the *Bacillus amyloliquefaciens* alpha-amylase gene (amyQ). Another example is a "consensus" promoter having the sequence TTGACA for the "−35" region and TATAAT for the "−10" region. Another example is the promoter of the *Bacillus licheniformis* penicillinase gene (penP). Another example are the promoters of the *Bacillus subtilis* xylA and xylB genes. Another example is the promoter of the *Bacillus thuringiensis* subsp. *tenebrionis* CryIIIA gene (cryIIIA, SEQ ID NO. 1) or portions thereof. Another example is the promoter of the prokaryotic beta-lactamase gene (Villa-Kamaroff et al., 1978, *Proceedings of the National Academy of Sciences USA* 75:3727-3731). Another example is the promoter of the spo1 bacterial phage promoter. Another example is the tac promoter (DeBoer et al., 1983, *Proceedings of the National Academy of Sciences USA* 80:21-25). Further promoters are described in "Useful proteins from recombinant bacteria" in *Scientific American* 242:74-94 (1980); and in Sambrook, Fritsch, and Maniatus, 1989, Molecular Cloning, A Laboratory Manual, 2d edition, Cold Spring Harbor, New York.

The two or more promoter sequences of the tandem promoter may simultaneously promote the transcription of the nucleic acid sequence. Alternatively, one or more of the promoter sequences of the tandem promoter may promote the transcription of the nucleic acid sequence at different stages of growth of the *Bacillus* cell.

In a preferred embodiment, the tandem promoter contains at least the amyQ promoter of the *Bacillus amyloliquefaciens* alpha-amylase gene. In another preferred embodiment, the tandem promoter contains at least a "consensus" promoter having the sequence TTGACA for the "−35" region and TATAAT for the "−10" region. In another preferred embodiment, the tandem promoter contains at least the amyL promoter of the *Bacillus licheniformis* alpha-amylase gene. In another preferred embodiment, the tandem promoter contains at least the cryIIIA promoter or portions thereof (Agaisse and Lereclus, 1994, supra).

In a more preferred embodiment, the tandem promoter contains at least the amyL promoter and the cryIIIA promoter. In another more preferred embodiment, the tandem promoter contains at least the amyQ promoter and the cryIIIA promoter. In another more preferred embodiment, the tandem promoter contains at least a "consensus" promoter having the sequence TTGACA for the "−35" region and TATAAT for the "−10" region and the cryIIIA promoter. In another more preferred embodiment, the tandem promoter contains at least two copies of the amyL promoter. In another more preferred embodiment, the tandem promoter contains at least two copies of the amyQ promoter. In another more preferred embodiment, the tandem promoter contains at least two copies of a "consensus" promoter having the sequence TTGACA for the "−35" region and TATAAT for the "−10" region. In another more preferred embodiment, the tandem promoter contains at least two copies of the cryIIIA promoter.

The construction of a "consensus" promoter may be accomplished by site-directed mutagenesis to create a promoter which conforms more perfectly to the established consensus sequences for the "−10" and "−35" regions of the vegetative "sigma A-type" promoters for *Bacillus subtilis* (Voskuil et al., 1995, *Molecular Microbiology* 17: 271-279). The consensus sequence for the "−35" region is TTGACA and for the "−10" region is TATAAT. The consensus promoter may be obtained from any promoter which can function in a *Bacillus* host cell.

In a preferred embodiment, the "consensus" promoter is obtained from a promoter obtained from the *E. coli* lac operon, *Streptomyces coelicolor* agarase gene (dagA), *Bacillus lentus* alkaline protease gene (aprH), *Bacillus licheniformis* alkaline protease gene (subtilisin Carlsberg gene), *Bacillus subtilis* levansucrase gene (sacB), *Bacillus subtilis* alpha-amylase gene (amyE), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus thuringiensis* subsp. *tenebrionis* CryIIIA gene (cryIIIA, SEQ ID NO. 1) or portions thereof, or prokaryotic beta-lactamase gene spo1 bacterial phage promoter.

In a more preferred embodiment, the "consensus" promoter is obtained from *Bacillus amyloliquefaciens* alpha-amylase gene (amyQ). In a most preferred embodiment, the consensus promoter is the "consensus" amyQ promoter contained in nucleotides 1 to 185 of SEQ ID NO. 3 or SEQ ID NO. 4. In another most preferred embodiment, the consensus promoter is the short "consensus" amyQ promoter contained in nucleotides 86 to 185 of SEQ ID NO. 3 or SEQ ID NO. 4. The "consensus" amyQ promoter of SEQ ID NO. 3 contains the following mutations of the nucleic acid sequence containing the wild-type amyQ promoter (SEQ ID NO. 2): T to A and T to C in the −35 region (with respect to the transcription start site) at positions 135 and 136, respectively, and an A to T change in the −10 region at position 156 of SEQ ID NO. 2. The "consensus" amyQ promoter (SEQ ID NO. 2) further contains a T to A change at position 116 approximately 20 base pairs upstream of the −35 region as shown in FIG. 21 (SEQ ID NO. 4). This change apparently had no detrimental effect on promoter function since it is well removed from the critical −10 and −35 regions.

Accordingly, in a preferred embodiment of any aspects of the invention, the heterologous promoter comprises two or more promoters; preferably the two or more promoters comprise one or more promoter derived from one or more *Bacillus* genes; more preferably the two or more promoters comprise one or more of the following: the amyQ promoter, the amyL promoter, the cryIIIA promoter, and a consensus promoter comprising the nucleotide sequence TTGACA for the −35 region and the nucleotide sequence TATAAT for the −10 region.

Site specific recombinases, including phage integrases, are well-known in the art, where they are usually grouped into tyrosine recombinases or serine recombinases. A subgroup of the serine recombinases are the large serine recombinases, which contains all the known serine recombinase-type phage integrases. The large serine recombinases contain the resolvase/invertase-like N-terminal catalytic domains of all serine recombinases, but their C-terminal regions are much larger and very diverse. (Smith and Thorpe, 2002, "Diversity in the serine recombinases", *Mol. Microbiol.* 44:299-307). A review of phage integrases is given by Groth and Calos (*J. Mol. Biol.* 335: 667-678 (2004)).

Accordingly, a preferred embodiment of all aspects of the invention relates to where the site specific recombinase comprises a phage integrase, preferably a tyrosine recombinase or a serine recombinase, more preferably a large serine recombinase, and most preferably the TP901-1 integrase.

The TP901-1 integrase is well-characterized, e.g., in Breüner et al., 2001, "Resolvase-like recombination performed by the TP901-1 integrase", *Microbiology* 147: 2051-2063. In addition, the recognition sequences of TP901-1 integrase (attP, attB, attL and attR) are well-known.

A preferred embodiment relates to the method of the first aspect, wherein RS1 comprises a nucleotide sequence at least 70%, preferably at least 75%, 80%, 85%, 90%, 95%, or most preferably at least 98% identical to $attB_{161}$ (SEQ ID NO: 21) or attBmin (SEQ ID NO: 22), RS2 comprises a nucleotide sequence at least 70%, preferably at least 75%, 80%, 85%, 90%, 95%, or most preferably at least 98% identical to attPmin (SEQ ID NO: 23), and the site specific recombinase comprises the phage TP901-1 integrase.

Since the attP and attB recognition sequences may be switched around, another preferred embodiment relates to the method of the first aspect, wherein RS1 comprises a nucleotide sequence at least 70%, preferably at least 75%, 80%, 85%, 90%, 95%, or most preferably at least 98% identical to attPmin (SEQ ID NO: 23), RS2 comprises a nucleotide sequence at least 70%, preferably at least 75%, 80%, 85%, 90%, 95%, or most preferably at least 98% identical to $attB_{161}$ (SEQ ID NO: 21) or attBmin (SEQ ID NO: 22), and the site specific recombinase comprises the phage TP901-1 integrase.

The attP and attB sequences may also be substituted with the corresponding attL and attR sequences in the method of the invention, which in turn may also be switched around, provided that the integrase is supplemented with the excisionase, Xis.

Accordingly, a preferred embodiment of the invention relates to the first aspect, wherein RS1 comprises a nucleotide sequence at least 70%, preferably at least 75%, 80%, 85%, 90%, 95%, or most preferably at least 98% identical to attLmin (SEQ ID NO: 24), RS2 comprises a nucleotide sequence at least 70%, preferably at least 75%, 80%, 85%, 90%, 95%, or most preferably at least 98% identical to attRmin (SEQ ID NO: 25), and the site specific recombinase comprises the phage TP901-1 integrase and excisionase Xis.

Another preferred embodiment of the invention relates to the first aspect, wherein RS1 comprises a nucleotide sequence at least 70%, preferably at least 75%, 80%, 85%, 90%, 95%, or most preferably at least 98% identical to attRmin (SEQ ID NO: 25), RS2 comprises a nucleotide sequence at least 70%, preferably at least 75%, 80%, 85%, 90%, 95%, or most preferably at least 98% identical to attLmin (SEQ ID NO: 24), and the site specific recombinase comprises the phage TP901-1 integrase and excisionase Xis.

Agaisse and Lereclus (*Molecular Microbiology* 13: 97-107 (1994)) disclose a structural and functional analysis of the promoter region involved in the full expression of the cryIIIA toxin gene of *Bacillus thuringiensis*. WO 94/25612 discloses an mRNA stabilizer region downstream of the promoter and upstream of the coding sequence of the cryIIIA gene which increases expression of the gene.

Hue et al. (*Journal of Bacteriology* 177: 3465-3471 (1995)) disclose a 5' mRNA stabilizer sequence which stabilized several heterologous RNA sequences when present at the 5' end and increased expression of downstream coding sequences several-fold in *Bacillus subtilis*.

"An mRNA processing/stabilizing sequence" is defined herein as a sequence located downstream of one or more promoter sequences and upstream of a coding sequence to which each of the one or more promoter sequences are operably linked such that all mRNAs synthesized from each promoter sequence may be processed to generate mRNA transcripts with a stabilizer sequence at the 5' end of the transcripts. The presence of such a stabilizer sequence at the 5' end of the mRNA transcripts increases their half-life (Agaisse and Lereclus, 1994, supra, Hue et al., 1995, supra). The mRNA processing/stabilizing sequence is complementary to the 3' extremity of a bacterial 16S ribosomal RNA. In a preferred embodiment, the mRNA processing/stabilizing sequence generates essentially single-size transcripts with a stabilizing sequence at the 5' end of the transcripts.

In a more preferred embodiment, the mRNA processing/stabilizing sequence is the *Bacillus thuringiensis* cryIIIA mRNA processing/stabilizing sequence disclosed in WO 94/25612 and Agaisse and Lereclus, 1994, supra, or portions thereof which retain the mRNA processing/stabilizing function. In another more preferred embodiment, the mRNA processing/stabilizing sequence is the *Bacillus subtilis* SP82 mRNA processing/stabilizing sequence disclosed in Hue et al., 1995, supra, or portions thereof which retain the mRNA processing/stabilizing function.

When the cryIIIA promoter and its mRNA processing/stabilizing sequence are employed in the methods of the present invention, a DNA fragment containing the sequence disclosed in WO 94/25612 and Agaisse and Lereclus, 1994, supra, or portions thereof which retain the promoter and mRNA processing/stabilizing functions, may be used. Furthermore, DNA fragments containing only the cryIIIA promoter or only the cryIIIA mRNA processing/stabilizing sequence may be prepared using methods well known in the art to construct various tandem promoter and mRNA processing/stabilizing sequence combinations. In this embodiment, the cryIIIA promoter and its mRNA processing/stabilizing sequence are preferably placed downstream of the other promoter sequence(s) constituting the tandem promoter and upstream of the coding sequence of the gene of interest.

In a preferred embodiment of the method of the first aspect of the invention, wherein at least one mRNA stabilizing region is located between the heterologous promoter and RS1 in the chromosome of the cell in step (a); preferably the at least one mRNA stabilizing region comprises a mRNA stabilizing region derived from cryIIIA; more preferably the at least one mRNA stabilizing region comprises a nucleotide sequence at least 70%, preferably at least 75%, 80%, 85%, 90%, 95%, or most preferably at least 98% identical to the sequence shown in positions 35-580 of SEQ ID NO: 26.

Another preferred embodiment relates to the method of the first aspect, wherein the polynucleotide construct further comprises at least one mRNA stabilizing region located upstream of the ORF or operon between the ORF or operon and RS2.

Another preferred embodiment relates to the cell of the second aspect, wherein at least one mRNA stabilizing region is located between the heterologous promoter and RS in the chromosome of the cell.

Yet another preferred embodiment relates to the cell of the third aspect, wherein at least one mRNA stabilizing region is located between the heterologous promoter and the one or more copies of the ORF or operon in the chromosome of the cell.

Preferably, in an embodiment of the polynucleotide construct of the fourth aspect, at least one mRNA stabilizing region is located upstream of the ORF or operon.

To be able to cross out the vector part of the integrated polynucleotide construct, including an optional marker, regions of homology can be designed at the proper positions in the construct and next to the recognition sequence in chromosome of the host cell prior to integration. This is illustrated by the regions designated "repeat" in FIG. 1. The regions may either be inserted heterologous polynucleotide regions, or one region may be designed on the basis of a corresponding region, which may be naturally found in the other sequence. Homologous recombination between these two regions subsequent to the integration of the plasmid via site specific recombination between the recognition sequences RS1 and RS2 will then lead to excision of the polynucleotide between the two regions, leaving only the ORF or operon of interest on the chromosome, next to the recognition sequence site resulting from the first integration event.

Accordingly, in a preferred embodiment of the method of the first aspect, the polynucleotide construct further comprises a region located upstream or downstream of the ORF or operon in the construct, said region being sufficiently homologous with a corresponding region located upstream or downstream, correspondingly, of RS1 in the chromosome of the cell to effectuate in vivo homologous recombination between the two homologous regions when both regions are present in the cell.

Alternatively, two regions that are recognition sites of a site specific recombinase, different from the one used for integration, can be inserted at the same positions as the before mentioned repeats. In the presence of the proper site specific recombinase recombination between the two sites will then lead to excision of the region between the two sites, leaving only the gene of interest on the chromosome.

Non-limiting examples are the well-known resolvase systems, with two res sites and a specific resolvase, which performs the recombination between the two sites. The concept of using site specific recombination systems for excision of sequences from the bacterial chromosome was described, e.g., for the recombination system of the broad-host range plasmid RP4 (Eberl et al., 1994, "Analysis of the multimer resolution system encoded by the parCBA operon of broad-host-range plasmid RP4", *Mol. Microbiol.* 12: 131-141)). Stark et al., 1992, "Catalysis by site-specific recombinases", *Trends in Genetics* 8: 432-439) is a review article on the mechanism of resolvase action. Camilli et al. ("Use of genetic recombination as a reporter of gene expression", *Proc. Natl. Acad. Sci. USA* 91: 2634-2638 ((1994)) describe the use of res sites and resolvase from the δγ-transposon in Vibrio cholera as a permanent, heritable marker of gene expression from a chromosomal gene. Chang et al. (("Construction of Tn917as1, a transposon useful for mutagenesis and cloning of *Bacillus subtilis* genes", *Gene* 150: 129-134 (1994)) describe the plasmids (pE194) containing erm-res-tnpA (transposase)-tnpR (resolvase) samt IR-res-ori colE1-ABR1-ABR2-IR (pD917; Tn917ac1).

The broad host range, gram-positive plasmid pAMβ1 (Clewell et al., 1974, "Characterization of three plasmid deoxyribonucleic acid molecules in a strain of *Streptococcus faecalis*: identification of a plasmid determining erythromycin resistance", *J. Bacteriol.* 117: 283-289) has been described to contain a resolution system, that resolves plasmid multimers into monomers via a site specific recombination event, requiring a specific plasmid encoded enzyme (resolvase) and a site, res, on the plasmid (Swinfield et al., 1991, "Characterization of a region of the *Enterococcus faecalis* plasmid pAMβ1 which enhances the segregational stability of pAMβ1-derived cloning vectors in *Bacillus subtilis*", *Plasmid* 26: 209-221; Janniere, L., Gruss, A., Ehrlich, S. D. (1993) Plasmids, pp. 625-644 in Sonenshein, A. L., Hoch, J. A., Losick, R. (eds.) *Bacillus subtilis* and other gram-positive bacteria: Biochemistry, Physiology and molecular genetics. American society for microbiology, Washington D.C.). It has been suggested to use a site-specific recombination system to remove a single selectable marker gene from the genome of a bacterial cell. For instance, Dale, et al. ("Gene transfer with subsequent removal of the selection gene from the host genome", *Proc. Natl. Acad. Sci. USA* 88: 10558-10562 (1991)) describe the use of the cre/lox system for removal of markers from transgenic plants and mentions that the use of this system would obviate the need for different selectable markers in subsequent rounds of gene tranfer into the same host. Kristensen et al., 1995, *J. Bacteriol.* 177: 52-58, describe the use of the multimer resolution system of the plasmid RP4 for the precise excision of chromosomal segments (such as marker genes introduced with heterologous DNA) from gram-negative bacteria. It is stated that the system is envisaged to be of interest in the generation of chromosomal insertions of heterologous DNA segments eventually devoid of any selection marker. WO 95/02058 describes a new transposon (tn5401) from *B. thuringiensis* containing transposase, resolvase, and res site. The transposon is used in a plasmid which contains *B. thuringiensis* DNA (e.g., origin and toxin gene) and, flanked by res sites, non-*B. thuringiensis* DNA (e.g., *E. coli* origin, selectable marker genes). The plasmid is introduced into *B. thuringiensis*. Subsequently, a plasmid expressing the resolvase is introduced (e.g., a thermosensitive plasmid containing the entrire transposon—but only used as resolvase donor) whereby the non-*B. thuringiensis* DNA is excised from the first plasmid.

To ease identification of the clones in which crossing out has taken place, a counterselectable marker, such as the ysbC gene (Danish patent application no. PA 2004 00227 filed Feb. 13, 2004 (Novozymes A/S)), can be present on the vector-part of the polynucleotide construct. When all the constructs integrated in the chromosomes have crossed out and are lost from the cell, the marker will no longer be present in the cell, which then becomes resistant to the selection.

Alternatively to a counterselectable marker, a gene that gives a screenable phenotype can be used, such as an antibiotic selection marker, GFP, or an amylase. Loss of all integrated constructs by excision will then lead to loss of resistance to the antibiotic, loss of green fluorescence, or loss of the amylase phenotype.

Accordingly, in a preferred embodiment of the first aspect, the polynucleotide construct further comprises at least one selectable marker, at least one counterselectable marker, or at least one screenable marker; preferably the at least one selectable marker, counterselectable marker, or the screenable marker is flanked on both sides by a recognition sequence(s) of a second site specific recombinase, preferably a resolvase.

The second aspect of the invention relates to a cell comprising in its chromosome one or more copies of a recognition sequence (RS) of a site specific recombinase, wherein each copy of the RS is located downstream of a copy of a heterologous promoter.

The third aspect of the invention relates to a cell comprising in its chromosome one or more copies of an open reading frame (ORF) or operon of interest, wherein each copy is under the transcriptional control of a heterologous promoter, and (i) wherein each copy of the ORF or operon is located in the chromosome upstream of a recognition sequence (RS) of a site specific recombinase, or (ii) wherein each copy of the ORF or operon is located in the chromosome downstream of a recognition sequence (RS) of a site specific recombinase.

The fourth aspect of the invention relates to a polynucleotide construct comprising a promoterless open reading frame (ORF) or operon encoding at least one polypeptide of interest, the construct also comprising a recognition sequence (RS) of a site specific recombinase located upstream or downstream of said ORF or operon.

In a preferred embodiment of the cell of second or third aspects, the polynucleotide of the fourth aspect, or the method of the final aspect, RS comprises a nucleotide sequence at least 70%, preferably at least 75%, 80%, 85%, 90%, 95%, or most preferably at least 98% identical to attB$_{161}$ (SEQ ID NO: 21), attBmin (SEQ ID NO: 22), or attPmin (SEQ ID NO: 23), and the site specific recombinase comprises the phage TP901-1 integrase; or RS comprises a nucleotide sequence at least 70%, preferably at least 75%, 80%, 85%, 90%, 95%, or most preferably at least 98% identical to attLmin (SEQ ID NO: 24) or attRmin (SEQ ID NO: 25), and the site specific recombinase comprises the phage TP901-1 integrase and excisionase Xis.

EXAMPLES

Materials and Methods
Strains
*Bacillus subtilis* DN1885 is described in Diderichsen et al., 1990, "Cloning of aldB, which encodes acetolactate decarboxylase, an exoenzyme from *Bacillus brevis*", *Journal of Bacteriology* 172: 4315-4321.

B. subtilis PL1801 is the B. subtilis DN1885 strain with disrupted apr and npr genes.

AEB43: B. subtilis PL1801 with a 161 bp attB fragment integrated in the xyl locus.

AEB165: AEB43 with the 43 bp minimal attB integrated in the amyE locus.

Primers:

```
pattB19DraIII (SEQ ID NO: 1):
CCCCCACTAAGTGCCTGACTTTCAACTAC pattB179NotI (SEQ ID NO: 2):
CCCCGCGGCCGCAAAAAAAGCAAAAAGC

PEP140 (SEQ ID NO: 3):
AATATTGGCCGGGGAAGCGGAAGAATGAAG

PEP218 (SEQ ID NO: 4):
CTATACTAGTCATCCTTGCAGGGTATGTTTC pamyE-EI (SEQ ID NO: 5):
GGGGGAATTCAACGGCCTCAACCTACTACTG M13-forward (SEQ ID NO: 6):
GTTTTCCCAGTCACGAC M13-revers (SEQ ID NO: 7):
CAGCTATGACCATGATTACGC pCI-5 (SEQ ID NO: 8):
CTTCTACCCATTATTACAGCAGGA pCI-9 (SEQ ID NO: 9):
AGTAGTTCGCCAGTTAATAGTTTG p1224seq-2 (SEQ ID NO: 10):
GCCATACAGCTACTCACTCG pPxyl-up (SEQ ID NO: 11):
CACTATGAATTCAGAAATACTCCTA pPxyl-down (SEQ ID NO: 12):
GATTGAGTCATGAGATTTCCCCCTTA pattPcry3A (SEQ ID NO: 13):
CTCGAGTCCAACTCGCTTAATTGCGAGTTTTTATTTCG
TTTATTTCAATTAAGGTA ATTAAAGATAATATCTTTG
AATTG pcry3AClaI (SEQ ID NO: 14):
ATCGATTGTTGTTTCATGATTCTCCTC pint-up (SEQ ID NO: 15):
GGGGTCATGACTAAGAAAGTAGCAATC pint-down (SEQ ID NO: 16):
GGGGAAGCTTAAGCGAGTTGGAATTTA pxylint-2 (SEQ ID NO: 17):
CAGGTCTTCTTCCGCCACTTG pM1632-1 (SEQ ID NO: 18):
AGCGAAAATGCCTCACA pattP-ExtTerm (SEQ ID NO: 19):
GGGGGGTACCTCCAACTCGCTTAATTGCGAGTTTTTAT
TTCGTTTATTTCAATTAAGGTAATTAAACCATGGCGGC
CGCTAGCGTCGACTAGTCAAAGATAGAAGAGCAGAGAG pTermBI (SEQ ID NO: 20):
CCCCGGATCCCCCGCGATACCGTCATTTTC
```

Plasmids pLB44: E. coli plasmid containing a 2 kb region of the phage TP901-1 genome, including the int gene and attP site (Christiansen et al., 1996. J. Bacteriol. 178(17): 5164-5173).

pBC16 is commercially available from DSMZ (DSM 4424); (Kreft et al., 1978, "Recombinant plasmids capable of replication in B. subtilis and E. coli", Mol. Gen. Genet. 162: 59-67).

pSJ2739 (described in U.S. Pat. No. 6,100,063) is derived from pE194, which is naturally temperature-sensitive for replication. The part of pSJ2739 which is relevant for this invention consists of the pE194 replicon, as well as a fragment derived from plasmid pUB110, enabling conjugation into B. licheniformis.

pAEB142: The int gene of TP901-1, encoding the phage integrase, is inserted after the xylose-inducible $P_{xyl}$ promoter in the pCR®-BluntII-TOPO® (Invitrogen) vector. The $P_{xyl}$ and int fragments were first amplified by two separate PCR-reactions. The $P_{xyl}$ fragment was obtained with chromosomal DNA from B. subtilis PL1801 as template and the primers were pPxyl-up & pPxyl-down, giving a fragment of 1.5 kb. To amplify the int gene, the plasmid pLB44 was used as template and the primers were pint-up & pint-down, again giving a fragment of 1.5 kb. The two fragments were digested with BspHI, joined by ligation, and used as template in a third PCR-reaction with primers pPxyl-up & pint-down, resulting in a fragment of 2.9 kb. This fragment was then inserted in the pCR®-BluntII-TOPO® vector in the Zero Blunt® TOPO® PCR cloning kit (Invitrogen).

pAEB146: The $P_{xyl}$-int fragment of pAEB142 was inserted in pSJ2739. This fragment was obtained by a two-step process, where the $P_{xyl}$ fragment and the upstream part of int is obtained from pAEB142 on a 1.7 EcoRI-HindIII-fragment and ligated to the 4.3 kb EcoRI-HindIII-fragment of pSJ2739, and subsequently the downstream part of int was obtained on a HindIII fragment from pAEB142 and inserted in the HindIII site of the first plasmid. pAEB146 contains erm gene, providing resistance to erythromycin (Em), and a temperature-sensitive replicon, as well as the factors required for conjugation, making it possible to use both in B. subtilis and B. licheniformis.

pAEB148: A PCR-fragment with the minimal attP ($attP_{min}$) and the cryIIIA region inserted in the pCR®-BluntII-TOPO® vector. The PCR fragment was obtained using primers pattPcry3A and pcry3AClaI, and the template was a plasmid containing the cryIIIA region. This gave a fragment of approximately 650 bp, which was cloned in the vector by using the Zero Blunt® TOPO® PCR cloning kit (Invitrogen).

pAEB153: A 636 bp attPmin-cryIIIA-fragment (SEQ ID NO: 26) was obtained from pAEB148 by digestion with XhoI and ClaI, and was inserted in the 2.1 kb SalI-ClaI fragment of pMOL1632. This plasmid contains the same replication origin as the integrase donor plasmid pAEB146 but does not encode the replication protein. Thus, replication of pAEB153 is dependent on donation of the replication protein from another vector, such as pAEB146, i.e., pAEB153 is a so-called "slave" of pAEB146.

pAEB267: A 360 bp fragment containing the minimal attP site of TP901-1 and a region of the B. licheniformis chromosome was obtained by PCR using primers pattP-ExtTerm and pTermBI, and chromosomal DNA from B. licheniformis as template. The fragment was digested with BamHI and KpnI and inserted in BamHI-KpnI digested pAEB146.

pAEB288: pAEB267 with an amylase encoding gene, amyL, which is inserted into an NcoI-NheI digested pAEB267.

Example 1

Construction of a *B. subtilis* Strain with Two TP901-1 attB Sites in the Chromosome As the first step, an 161 bp attB site (attB$_{161}$, SEQ ID NO:21) was integrated in the xyl locus in *B. subtilis* strain PL1801, resulting in the strain AEB43. Integration was obtained by double cross-over of a DNA fragment which contains attB$_{161}$ adjacent to the cat gene, surrounded by an upstream and a downstream region of the xyl locus. The upstream and downstream xyl fragments were obtained with PCR on chromosomal DNA from *B. subtilis* using primers that are suitable for amplifying regions of sufficient size for an efficient integration by homologous recombination (0.5 kb or more). By PCR, these fragments were joined with the attB$_{161}$ fragment (obtained from *Lactococcus lactis* subsp. *cremoris* 3107) and with the cat gene, yielding chloramphenicol (Cm) resistance.

This xylup-attB-cat-xyldown fragment was introduced into PL1801 by transformation and the transformants were plated on Cm containing plates. Cells in which recombination between the DNA-fragment and the chromosome had occurred in both xyl regions would have retained the cat gene and would thus be Cm$^R$. Transformants with this phenotype were isolated and by PCR and sequencing they were found to have the attB$_{161}$ site integrated in the xyl locus.

Secondly, the minimal attB site of 43 bp (attB$_{min}$, Breüner et al., 2001, *Microbiology* 147: 2051-2063; SEQ ID NO: 22) was integrated in the amyE locus in AEB43, resulting in strain AEB165, which had two functional versions or copies of the TP901-1 attB site integrated in the chromosome, attB$_{161}$ and attB$_{min}$. Integration of attB$_{min}$ was obtained by transformation and subsequent double cross-over into the chromosome of AEB43 of the amyup-tet-attB-amydown PCR fragment, which was obtained much as described for integration of attB$_{161}$ in the xyl locus, except that upstream and downstream regions of the amyE locus were flanking the tet-attB-fragment, and these regions were obtained by PCR from pBC16 with the primers pattB-tet & ptet-down.

When this fragment was transformed into AEB43 Tc$^R$ transformants could only arise if double crossover took place between the PCR-fragment and the bacterial chromosome at both ends of the PCR-fragment, leaving the tet gene and attB$_{min}$ in the chromosome. A number of Tc$^R$ transformants were isolated and found by PCR to contain the attB$_{min}$ site integrated at the intended position in the amyE locus.

Example 2

Construction of an Integrase-Donor Plasmid

The TP901-1 integrase is needed to perform the recombination between the attB and attP sites. The expression of the integrase can be placed under the control of a constitutive or an inducible promoter. In plasmid pAEB146 expression of the integrase is under the control of the P$_{xyl}$-promoter, which is induced from a low to a high level of activity upon the addition of xylose. pAEB146 has a temperature sensitive replicon functional in *Bacillus* and the oriT region from plasmid pUB110 which enables conjugation, and thus can be used in both *B. subtilis* and *B. licheniformis*. Alternatively, the integrase can be expressed from a plasmid which has a different kind of replicon, or it could be integrated into the chromosome.

Example 3

Construction of an attP Plasmid pAEB153 contains the minimal attP site of TP901-1 (SEQ ID NO: 23) determined in Brøndsted and Hammer, 1999, *App. Environ. Microbiol.* 65: 752-758, but a larger attP region can also be used, or a smaller, if it is still active in recombination. Replication of pAEB153 is dependent on donation of replication protein from another plasmid with the pE194 replicon such as pAEB146. Alternatively the attP site can be cloned on a different plasmid vector, e.g., one with an origin which is not dependent on other plasmids for replication, and/or a thermosensitive origin. The attP site can also be included on the plasmid from which integrase is expressed.

The plasmid containing attP can be used as a vector for cloning genes in such a way, that integration of the plasmid in attB in the chromosome will lead to expression of the gene from a promoter present in the chromosome next to the attB site. We therefore included the mRNA-stabilizing cryIIIA region in pAEB153 to obtain maximal expression of said gene. To make the distance between the promoter and the cryIIIA region as short as possible attP$_{min}$ and cryIIIA are overlapping. To obtain optimal overlap a single base in the attP region was changed. The mutation in attP did not interfere with the ability of the region to participate in recombination with attB, as is shown in example 5.

Example 4

Integration in Both Copies of attB Simultaneously

AEB165 (2×attB) was transformed with pAEB146 (Int-donor) resulting in strain AEB182. AEB182 was in turn transformed with pAEB153 (attP). Transformants were grown and streaked at 33° C. (permissive temperature) and with selection for both plasmids to allow recombination between the attP and attB sites to take place. Then, a number of colonies were streaked on plates with selection only for pAEB153 and the incubation temperature was increased to 50° C., which disables replication of pAEB146 and thereby also of pAEB153. The only cells that can grow under these conditions are the ones where pAEB153 has integrated into the chromosome. The isolates were also checked for the presence of the Int-donor plasmid pAEB146 by streaking on selective plates (Em).

Eight colonies were streaked in this way, and six of the isolates were found both to be able to grow at 50° C. and to have lost the Int donor. Recombination between attP and attB was checked by PCR on chromosomal DNA from these six strains. Both the presence of the intact attB sites and of the attL site (SEQ ID NO:24), which is the result of recombination between attB and attP was investigated. The primers used are shown in Table 1 and the results of the PCR-reactions are summarized in Table 2.

TABLE 1

| primers used to check recombination | | |
|---|---|---|
| Site | xyl-locus | amyE-locus |
| attB | pxylint-2 & pCl-5 | pamy-1 & ptet-1 |
| attL | pM1632-1 & pxylint-2 | pM1632-1 & pamy-1 |

TABLE 2

PCR-checks on the integration-strains

| | AEB182/pAEB153 | | | | | |
|---|---|---|---|---|---|---|
| PCR-fragment | A | B | C | D | E | F |
| attB$_{161}$ in xyl | ✓ | — | — | — | ✓ | — |
| attL in xyl | — | ✓ | ✓ | ✓ | — | ✓ |
| attB$_{min}$ in amyE | — | ✓ | — | — | ✓ | ✓ |
| attL in amyE | ✓ | — | ✓ | ✓ | — | — |

✓: a PCR fragment of the correct size was observed.
—: a PCR fragment of the correct size was not observed.

Integration of pAEB153 had occurred in the following attB sites: A: in amyE; B: in xyl; C and D: in both sites; E: in none of the attB sites; and F: in xyl. Thus, double integration occurred in two out of the six strains tested.

This experiment was performed without the addition of xylose to the medium. To increase integration efficiency further, the production of integrase could be increased by adding xylose and thereby activating the R$_{xyl}$ promoter, leading to a higher expression of the integrase. The xylose concentration could, e.g., be between 0.05 and 5%; at high concentrations of xylose the integrase is overexpressed and becomes toxic to the cell.

Example 5

Identification of Cells where Integration in All attB Sites has Taken Place

To ease identification of cells where the attP plasmid has integrated site-specifically in all available attB sites, a counterselectable marker such as the ysbC gene (Danish patent application no. PA 2004 00227 filed Feb. 13, 2004) can be positioned downstream of a promoter next to all the attB sites in the chromosomes, but separated from the promoter by the attB site. Expression of the counterselectable marker from the promoter will lead to the cell being sensitive to the selective pressure (with ysbC. fluoro-orotate). When integration of the attP plasmid happens in such an attB site, the counterselectable marker is separated from the promoter, and the marker will no longer be expressed from this locus. However only when integration has occurred in all attB sites will no marker be produced, and the the cell will become resistant to the selection.

Alternatively to a counterselectable marker, a gene that gives a screenable phenotype can be used, such as an antibiotic selection marker, green fluorescence protein (GFP), beta-galactosidase, an amylase, or others. Integration of the attP plasmid in all of the attB sites will then lead to loss of resistance to the antibiotic, of green fluorescence, of colour on X-gal plates, of the amylase phenotype, or of what other phenotype was expressed from the marker.

Example 6

The attB and attP Sites are Interchangeable

In a manner similar to the one described in the above examples, the sites can be interchanged, so that one or more attP sites are inserted in the host genome, and the attB site is present in a vector to be integrated into the attP sites on the chromosome.

In another setup attP and attB can be exchanged with copies of attL (SEQ ID NO:24) in the chromosome of the host and attR (SEQ ID NO:25) on the plasmid; or vice versa. Recombination between the attL and attR sites will results in the creation of attP and attB sites after recombination. However, effective recombination of the TP901-1's attL and attR sites requires the presence of the excisionase, Xis, in addition to the integrase (Breüner et al., 1990, "Novel Organization of Genes Involved in Prophage Excision Identified in the Temperate Lactococcal Bacteriophage TP901-1". *J. Bacteriol.* 181(23): 7291-7297.

Example 7

Construction of a Strain with One or More attB Sites in the Genome, Each Adjacent to One or More Promoters Using an approach similar to the one described in example 1, attB sites were inserted at several positions in the chromosome of *B. licheniformis*, each site was inserted along with and downstream of a heterologous tandem promoter (as disclosed in WO 99/43835). A vector comprising an attP site and an amylase encoding gene was then integrated into the chromosomal attB site by the integrase. The orientation of the amylase gene in the vector with respect to the attP site ensured that the gene became operably linked with the tandem promoter, when the vector was integrated into the chromosome through the recombination of the attB and attP sites.

The amylase encoding gene was inserted in the attP-int containing plasmid pAEB267 in such a way that integration of the plasmid via site-specific recombination between attB and attP catalysed by the TP901-1 integrase would result in the amylase gene being inserted into the chromosome so that it would be expressed from the heterologous tandem promoter, separated from the gene by the attL site (FIG. 1) after the recombination. A strain where such an integration event had taken place (verified by PCR as described in example 4) was streaked on amylose containing plates, and clearing zones were formed, demonstrating that the amylase was expressed from the tandem promoter next to the attL site. No clearing zones were observed when pAEB267 without amylase gene was integrated in a similar manner as a control.

Example 8

Construction of a Strain with Three Copies of an Amylase Gene in the Genome, Each Adjacent to a Promoter Using an approach similar to the one described in example 1, but adapted to *B. licheniformis* in design of the primers and chromosomal fragments used, attB$_{min}$ sites were inserted at three positions in the chromosome of *B. licheniformis* (the amyL, xyl and gnt loci). Each attB$_{min}$ site was inserted along with and downstream of a heterologous tandem promoter (disclosed in WO 99/43835). A vector comprising the corresponding attP site and an amylase encoding gene, designed as the plasmid in FIG. 2 with the amylase in the place of "genX", was then integrated into all the chromosomal attB sites by the integrase. The cryIIIA region was located upstream of the amylase gene, and the orientation of the amylase gene in the vector with respect to the attP site ensured that the gene was located and oriented in all three loci as shown for "genX" in the middle part of FIG. 2. Subsequent crossing out of the vectorparts of the integrated plasmids in all three loci by means of homologous recombination between the two cryIIIA regions in each locus resulted in a strain, in which each of the three loci contained the region shown in the bottom of FIG. 2: promoter, cryIIIA, amylase, and attR.

The invention claimed is:

1. A method of constructing a recombinant cell comprising in its chromosome two or more copies of an open reading frame (ORF) or operon, wherein the two or more copies encode that same polypeptide of interest, wherein each copy being under the transcriptional control of a heterologous promoter, and wherein the cell comprises two or more identical copies of a recombined TP901-1 integrase recognition sequence, said method comprising the steps of:
   (a) providing a cell comprising in its chromosome two or more copies of a first recognition sequence (RS1) of a TP901-1 integrase, wherein each copy of RS1 is located downstream of a copy of said heterologous promoter;
   (b) introducing into said cell a polynucleotide construct comprising the ORF or operon and a second recognition sequence (RS2) of the TP901-1 integrase, where RS2 is located and oriented with respect to the ORF or operon so that an in vivo recombination of RS2 with a copy of RS1 in the chromosome of the cell will integrate the construct into the chromosome and place the ORF or operon downstream of and in the same orientation as the heterologous promoter; and
   (c) recombining RS2 with the two or more copies of RS1 in the presence of the TP901-1 integrase, whereby two or more copies of the ORF or operon are simultaneously integrated into the chromosome and placed:
       (i) either directly under the transcriptional control of the heterologous promoter, or
       (ii) downstream of and in the same orientation as the heterologous promoter but separated from it by a region, which can be excised after one or more optional recombination events, whereby the ORF or operon of interest is placed under the transcriptional control of the heterologous promoter.

2. The method of claim 1, wherein the cell is a prokaryotic cell.

3. The method of claim 2, wherein the prokaryotic cell is a *Bacillus* cell.

4. The method of claim 3, wherein the *Bacillus* cell is a *B. subtilis* or a *B. licheniformis* cell.

5. The method of claim 1, wherein the ORF or operon encodes at least one enzyme.

6. The method of claim 5, wherein the ORF or operon encodes an oxidoreductase, a transferase, a hydrolase, a lyase, an isomerase, or a ligase.

7. The method of claim 6, wherein the ORF or operon encodes an amylase.

8. The method of claim 1, wherein the heterologous promoter comprises two or more promoters.

9. The method of claim 8, wherein the two or more promoters comprise one or more promoters derived from one or more *Bacillus* genes.

10. The method of claim 8, wherein the two or more promoters comprise one or more of the following: the amyQ promoter, the amyL promoter, the cryIIIA promoter, and a consensus promoter comprising the nucleotide sequence TTGACA for the −35 region and the nucleotide sequence TATAAT for the −10 region.

11. The method of claim 1, wherein RS1 comprises a nucleotide sequence at least 70% identical to $attB_{161}$ (SEQ ID NO: 21) or attBmin (SEQ ID NO: 22), RS2 comprises a nucleotide sequence at least 70% identical to attPmin (SEQ ID NO: 23).

12. The method of claim 1, wherein RS1 comprises a nucleotide sequence at least 70% identical to attPmin (SEQ ID NO: 23), RS2 comprises a nucleotide sequence at least 70% identical to $attB_{161}$ (SEQ ID NO: 21) or attBmin (SEQ ID NO: 22).

13. The method of claim 1, wherein RS1 comprises a nucleotide sequence at least 70% identical to attLmin (SEQ ID NO: 24), RS2 comprises a nucleotide sequence at least 70% identical to attRmin (SEQ ID NO: 25), and step (c) further comprises excisionase Xis.

14. The method of claim 1, wherein RS1 comprises a nucleotide sequence at least 70% identical to attRmin (SEQ ID NO: 25), RS2 comprises a nucleotide sequence at least 70% identical to attLmin (SEQ ID NO: 24), and step (c) further comprises excisionase Xis.

15. The method of claim 1, wherein at least one mRNA stabilizing region is located between the heterologous promoter and RS1 in the chromosome of the cell in step (a).

16. The method of claim 15, wherein the at least one mRNA stabilizing region comprises a mRNA stabilizing region derived from cryIIIA.

17. The method of claim 16, wherein the at least one mRNA stabilizing region comprises a nucleotide sequence at least 70% identical to the sequence shown in positions 35-580 of SEQ ID NO: 26.

18. The method of claim 1, wherein the polynucleotide construct further comprises at least one mRNA stabilizing region located upstream of the ORF or operon between the ORF or operon and RS2.

19. The method of claim 18, wherein the at least one mRNA stabilizing region comprises a mRNA stabilizing region derived from cryIIIA.

20. The method of claim 19, wherein the at least one mRNA stabilizing region comprises a nucleotide sequence at least 70% identical to the sequence shown in positions 35-580 of SEQ ID NO: 26.

21. The method of claim 1, wherein the polynucleotide construct further comprises a region located upstream or downstream of the ORF or operon in the construct, said region being sufficiently homologous with a corresponding region located upstream or downstream, correspondingly, of RS1 in the chromosome of the cell to effectuate in vivo homologous recombination between the two homologous regions when both regions are present in the cell.

22. The method of claim 1, wherein the polynucleotide construct further comprises at least one selectable marker, at least one counterselectable marker, or at least one screenable marker.

23. The method of claim 22, wherein the selectable marker, the counterselectable marker or the screenable marker is flanked on both sides by a recognition sequence(s) of a second site specific recombinase.

* * * * *

SEQUENCE LISTING

<160> NUMBER OF SEQ ID NOS: 26

<210> SEQ ID NO 1
<211> LENGTH: 29
<212> TYPE: DNA
<213> ORGANISM: Artificial sequence
<220> FEATURE:
<223> OTHER INFORMATION: Primer

<400> SEQUENCE: 1
cccccactaa gtgcctgact ttcaactac                29

<210> SEQ ID NO 2
<211> LENGTH: 28
<212> TYPE: DNA
<213> ORGANISM: Artificial sequence
<220> FEATURE:
<223> OTHER INFORMATION: Primer

<400> SEQUENCE: 2
ccccgcggcc gcaaaaaaag caaaaagc                28

<210> SEQ ID NO 3
<211> LENGTH: 30
<212> TYPE: DNA
<213> ORGANISM: Artificial sequence
<220> FEATURE:
<223> OTHER INFORMATION: Primer

<400> SEQUENCE: 3
aatattggcc ggggaagcgg aagaatgaag                30

<210> SEQ ID NO 4
<211> LENGTH: 31
<212> TYPE: DNA
<213> ORGANISM: Artificial sequence
<220> FEATURE:
<223> OTHER INFORMATION: Primer

<400> SEQUENCE: 4
ctatactagt catccttgca gggtatgttt c                31

<210> SEQ ID NO 5
<211> LENGTH: 31
<212> TYPE: DNA
<213> ORGANISM: Artificial sequence
<220> FEATURE:
<223> OTHER INFORMATION: Primer

<400> SEQUENCE: 5
gggggaattc aacggcctca acctactact g                31

<210> SEQ ID NO 6
<211> LENGTH: 17
<212> TYPE: DNA
<213> ORGANISM: Artificial sequence
<220> FEATURE:
<223> OTHER INFORMATION: Primer

<400> SEQUENCE: 6
gttttcccag tcacgac                17

<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7
cagctatgac catgattacg c                                          21

<210> SEQ ID NO 8
<211> LENGTH: 24
<212> TYPE: DNA
<213> ORGANISM: Artificial sequence
<220> FEATURE:
<223> OTHER INFORMATION: Primer

<400> SEQUENCE: 8
cttctaccca ttattacagc agga                                       24

<210> SEQ ID NO 9
<211> LENGTH: 24
<212> TYPE: DNA
<213> ORGANISM: Artificial sequence
<220> FEATURE:
<223> OTHER INFORMATION: Primer

<400> SEQUENCE: 9
agtagttcgc cagttaatag tttg                                       24

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
gccatacagc tactcactcg                                            20

<210> SEQ ID NO 11
<211> LENGTH: 25
<212> TYPE: DNA
<213> ORGANISM: Artificial sequence
<220> FEATURE:
<223> OTHER INFORMATION: Primer

<400> SEQUENCE: 11
cactatgaat tcagaaatac tccta                                      25

<210> SEQ ID NO 12
<211> LENGTH: 26
<212> TYPE: DNA
<213> ORGANISM: Artificial sequence
<220> FEATURE:
<223> OTHER INFORMATION: Primer

<400> SEQUENCE: 12
gattgagtca tgagatttcc ccctta                                     26

<210> SEQ ID NO 13
<211> LENGTH: 80
<212> TYPE: DNA
<213> ORGANISM: Artificial sequence
<220> FEATURE:
<223> OTHER INFORMATION: Primer

```
<400> SEQUENCE: 13
ctcgagtcca actcgcttaa ttgcgagttt ttatttcgtt tatttcaatt aaggtaatta      60
aagataatat ctttgaattg                                                  80

<210> SEQ ID NO 14
<211> LENGTH: 27
<212> TYPE: DNA
<213> ORGANISM: Artificial sequence
<220> FEATURE:
<223> OTHER INFORMATION: Primer

<400> SEQUENCE: 14
atcgattgtt gtttcatgat tctcctc                                          27

<210> SEQ ID NO 15
<211> LENGTH: 27
<212> TYPE: DNA
<213> ORGANISM: Artificial sequence
<220> FEATURE:
<223> OTHER INFORMATION: Primer

<400> SEQUENCE: 15
ggggtcatga ctaagaaagt agcaatc                                          27

<210> SEQ ID NO 16
<211> LENGTH: 27
<212> TYPE: DNA
<213> ORGANISM: Artificial sequence
<220> FEATURE:
<223> OTHER INFORMATION: Primer

<400> SEQUENCE: 16
ggggaagctt aagcgagttg gaattta                                          27

<210> SEQ ID NO 17
<211> LENGTH: 21
<212> TYPE: DNA
<213> ORGANISM: Artificial sequence
<220> FEATURE:
<223> OTHER INFORMATION: Primer

<400> SEQUENCE: 17
caggtcttct tccgccactt g                                                21

<210> SEQ ID NO 18
<211> LENGTH: 17
<212> TYPE: DNA
<213> ORGANISM: Artificial sequence
<220> FEATURE:
<223> OTHER INFORMATION: Primer

<400> SEQUENCE: 18
agcgaaaatg cctcaca                                                     17

<210> SEQ ID NO 19
<211> LENGTH: 161
<212> TYPE: DNA
<213> ORGANISM: Artificial sequence
<220> FEATURE:
<223> OTHER INFORMATION: Primer

<400> SEQUENCE: 19
gtgcctgact ttcaactact ttaactactg ctgcttcacc agttttttga acttgtgctt      60
```
tttcttttat caaatttggc acaaaaagca aaattaaaat actgataatt gccaacacaa    120
ttaacatctc aatcaaggta aatgcttttt gctttttttg c    161

```
<210> SEQ ID NO 20
<211> LENGTH: 43
<212> TYPE: DNA
<213> ORGANISM: Artificial sequence
<220> FEATURE:
<223> OTHER INFORMATION: Primer

<400> SEQUENCE: 20
```
ctgataattg ccaacacaat taacatctca atcaaggtaa atg    43

```
<210> SEQ ID NO 21
<211> LENGTH: 161
<212> TYPE: DNA
<213> ORGANISM: Artificial sequence
<220> FEATURE:
<223> OTHER INFORMATION: attB161 site

<400> SEQUENCE: 21
```
gtgcctgact ttcaactact ttaactactg ctgcttcacc agttttttga acttgtgctt    60
tttcttttat caaatttggc acaaaaagca aaattaaaat actgataatt gccaacacaa    120
ttaacatctc aatcaaggta aatgcttttt gctttttttg c    161

```
<210> SEQ ID NO 22
<211> LENGTH: 43
<212> TYPE: DNA
<213> ORGANISM: Artificial sequence
<220> FEATURE:
<223> OTHER INFORMATION: attBmin site

<400> SEQUENCE: 22
```
ctgataattg ccaacacaat taacatctca atcaaggtaa atg    43

```
<210> SEQ ID NO 23
<211> LENGTH: 56
<212> TYPE: DNA
<213> ORGANISM: Artificial sequence
<220> FEATURE:
<223> OTHER INFORMATION: attPmin site

<400> SEQUENCE: 23
```
tccaactcgc ttaattgcga gttttttattt cgtttatttc aattaaggta actaaa    56

```
<210> SEQ ID NO 24
<211> LENGTH: 45
<212> TYPE: DNA
<213> ORGANISM: Artificial sequence
<220> FEATURE:
<223> OTHER INFORMATION: attLmin site

<400> SEQUENCE: 24
```
ctgataattg ccaacacaat taacatctca attaaggtaa ctaaa    45

```
<210> SEQ ID NO 25
<211> LENGTH: 54
<212> TYPE: DNA
<213> ORGANISM: Artificial sequence
<220> FEATURE:
<223> OTHER INFORMATION: attRmin site

<400> SEQUENCE: 25
```
tccaactcgc ttaattgcga gttttttattt cgtttatttc aatcaaggta aatg    54

```
<210> SEQ ID NO 26
<211> LENGTH: 636
<212> TYPE: DNA
<213> ORGANISM: Artificial sequence
<220> FEATURE:
<223> OTHER INFORMATION: attPmin-cryIIIA-fragment cloned in pAEB153
<220> FEATURE:
<221> NAME/KEY: misc_feature
<222> LOCATION: (35)..(580)
<223> OTHER INFORMATION: cryIIIa derived mRNA stabilizing region

<400> SEQUENCE: 26
atcgattgtt gtttcatgat tctcctcccc caatgagctc cataatacat aattttcaaa      60
ctgataaaat gatttttcat aaatccatta gacggtgcaa atatatgttt ttaatgttct     120
tcgtttttag gcatccctcc tttcaagata aataatttat acactattct attggaatct    180
taatcattcc aatagaaaaa tatgtaatga ttataaataa gtcgcttctt atcataaata    240
tatttacata ttcatttaat actacatcat gttaggtata gtaaggctat caagggtgtc    300
ttaatttcta cttgtaacaa tgtattggca tattatatat tgaattgaga aaattaaata    360
cagcgataat tcacatgaac aagttcattg gtagttatat tttcaaattt tcaaggttgt    420
gcttgtatgt cattctatag ttagataagc atttgaggta gagtccgtcc gaatatattt    480
gtaatctgaa gaaggttcaa acatatttct atataacgta ttcttttttt gtagttctta    540
cttttgaggg gcgttacaat tcaaagatat tatctttaat taccttaatt gaaataaacg    600
aaataaaaac tcgcaattaa gcgagttgga ctcgag                              636
```